United States Patent
Sidlesky

(10) Patent No.: US 11,540,706 B2
(45) Date of Patent: Jan. 3, 2023

(54) METHOD OF USING A MANUALLY-OPERATED LIGHT PLANE GENERATING MODULE TO MAKE ACCURATE MEASUREMENTS OF THE DIMENSIONS OF AN OBJECT SEEN IN AN IMAGE TAKEN BY AN ENDOSCOPIC CAMERA

(71) Applicant: V.T.M. (Virtual Tape Measure) Technologies Ltd., Atlit (IL)

(72) Inventor: Avishay Sidlesky, Atlit (IL)

(73) Assignee: V.T.M. (Virtual Tape Measure) Technologies Ltd., Atlit (IL)

( * ) Notice: Subject to any disclaimer, the term of this patent is extended or adjusted under 35 U.S.C. 154(b) by 678 days.

(21) Appl. No.: 16/494,529

(22) PCT Filed: Apr. 11, 2018

(86) PCT No.: PCT/IL2018/050415
§ 371 (c)(1),
(2) Date: Sep. 16, 2019

(87) PCT Pub. No.: WO2018/189742
PCT Pub. Date: Oct. 18, 2018

(65) Prior Publication Data
US 2021/0121053 A1    Apr. 29, 2021

Related U.S. Application Data

(60) Provisional application No. 62/485,267, filed on Apr. 13, 2017.

(51) Int. Cl.
*A61B 1/018* (2006.01)
*A61B 90/00* (2016.01)
(Continued)

(52) U.S. Cl.
CPC ............ *A61B 1/018* (2013.01); *A61B 1/0005* (2013.01); *A61B 1/00009* (2013.01);
(Continued)

(58) Field of Classification Search
CPC .................................................. A61B 2576/00
See application file for complete search history.

(56) References Cited

U.S. PATENT DOCUMENTS 9,179,822 B2    11/2015    Kitamura et al.
9,545,220 B2     1/2017    Sidlesky
(Continued)

FOREIGN PATENT DOCUMENTS

CN    102341054 A     2/2012
CN    102811655 A    12/2012
(Continued)

OTHER PUBLICATIONS

International Search Report issued in PCT Patent Application No. PCT/IL2018/050415 dated Jul. 19, 2018.
(Continued)

*Primary Examiner* — John P Leubecker
(74) *Attorney, Agent, or Firm* — Marshall, Gerstein & Borun LLP

(57) ABSTRACT

Presented herein is a method of using a manually-operated light plane generating module to make accurate measurements of the dimensions of an object seen in an image taken by an endoscopic camera. The method comprises: providing the light plane generating module with distinctive features, introducing the light plane generating module until the distinctive features are visible in the image, aligning the light plane across the object, and providing a processor device and software configured to analyze the camera images. Also described are diagnostic or therapeutic endoscopic tools that comprise an attached light plane generating
(Continued)

module to provide the tool with integrated light plane measurement capabilities, wherein the tool is configured to be used in the described method.

6 Claims, 5 Drawing Sheets

(51) Int. Cl.
*A61B 1/00* (2006.01)
*A61B 1/06* (2006.01)

(52) U.S. Cl.
CPC ............ *A61B 1/0676* (2013.01); *A61B 90/36* (2016.02); *A61B 2090/365* (2016.02)

(56) References Cited

U.S. PATENT DOCUMENTS

| | | | |
|---|---|---|---|
| 2009/0048611 A1* | 2/2009 | Funda | B25J 17/0275 606/130 |
| 2012/0327186 A1* | 12/2012 | Kitamura | A61B 6/5247 348/45 |
| 2015/0161802 A1* | 6/2015 | Christiansen | A61B 90/06 348/74 |
| 2016/0066768 A1 | 3/2016 | Popovic et al. | |
| 2016/0287141 A1 | 10/2016 | Sidlesky | |
| 2017/0238962 A1* | 8/2017 | Hansen | A61B 1/05 |
| 2017/0251900 A1* | 9/2017 | Hansen | G06T 19/20 |
| 2018/0071032 A1* | 3/2018 | de Almeida Barreto | G06T 19/006 |
| 2019/0008603 A1* | 1/2019 | Hansen | A61B 34/20 |

FOREIGN PATENT DOCUMENTS

| | | | | |
|---|---|---|---|---|
| CN | 105078580 A | 11/2015 | | |
| CN | 105188594 A | 12/2015 | | |
| JP | H3128043 A | 5/1991 | | |
| JP | 2008194156 A | 8/2008 | | |
| JP | 201723562 A | 2/2017 | | |
| JP | 2017508529 A | 3/2017 | | |
| WO | WO-2010061293 A2 * | 6/2010 | ......... | A61B 1/00057 |
| WO | WO-2010078016 A1 | 7/2010 | | |
| WO | WO-2016/154557 A1 | 9/2016 | | |
| WO | WO-2017054817 A1 * | 4/2017 | | |
| WO | WO-2017059860 A1 * | 4/2017 | ........... | A61B 1/0005 |

OTHER PUBLICATIONS

Written Opinion issued in PCT Patent Application No. PCT/IL2018/050415 dated Jul. 19, 2018.
Notice of First Review Opinion, Application No. CN 2018800249218, Chinese Intellectual Property Office, dated Mar. 9, 2022.
Notice of Reasons for Refusal, Application No. JP 2019-556260, Japanese Patent Office, dated Mar. 10, 2022.

* cited by examiner

METHOD OF USING A MANUALLY-OPERATED LIGHT PLANE GENERATING MODULE TO MAKE ACCURATE MEASUREMENTS OF THE DIMENSIONS OF AN OBJECT SEEN IN AN IMAGE TAKEN BY AN ENDOSCOPIC CAMERA

FIELD OF THE INVENTION

The invention is from the field of medical devices. Specifically the invention relates to endoscopic devices comprising visualization systems. More specifically the invention relates to methods for determining the position and orientation of medical tools inserted through a working channel of the endoscopic device or through a trocar and visible in images gathered by the visualization systems and methods for conducting measurements with said tools.

BACKGROUND OF THE INVENTION

When using a camera equipped borescope to inspect engines or machined parts for imperfections of interior surfaces, it would be advantageous to be able to perform and record accurate, three-dimensional measurements to obtain the dimensions of the imperfections in order to be able to evaluate the extent of the damage and to determine what corrective measures should be taken.

During endoscopic medical procedures, it is of an advantage to perform accurate three dimensional measurements to obtain dimensions of anatomical structures within the lumen, such as lesions, stenoses, tumors, and the like. Tracking such measurements along time may further improve the level of care provided.

Currently, physicians using a state of the art endoscope, be it flexible or rigid, monocular or stereoscopic, do not have a true volumetric perspective within the acquired image and are unable to conduct accurate measurements. A common practice is to place a tool of known size (e.g., a catheter with known diameter) next to the anatomical structure and use it as a scale to assess dimensions. Because the tool is being freely manipulated by hand distortions in the images that affect the accuracy of the measurements such as foreshortening take place.

In U.S. Pat. No. 9,545,220 the inventor of the present invention disclosed a system and method for measuring 3D distances and dimensions of objects in endoscopic images by using a light plane to make Euclidean and geodesic measurements. The endoscopic measurement system of the invention comprises a flexible or rigid endoscopic device equipped with standard visualization systems and a module containing components for generating a light plane. Based on triangulation, the intersection curve between the light plane and the object of interest is measureable in 3D in the coordinate system of the visualization systems.

In U.S. Pat. No. 9,545,220 embodiments are described in which the light plane generating module can be provided as either a dedicated component of an endoscopic device or as an add-on unit that can be attached and detached from an endoscopic device. To enable correction for distortions and insure accurate measurements calibration must be carried out to know the location and orientation of the light plane relative to the focal point of the camera. For the dedicated embodiment the calibration is carried out in the factory during manufacture of the device. For the add-on embodiment a calibration is made before each procedure, which can be carried out automatically with a docking station, which is described therein.

In U.S. Pat. No. 9,545,220 a third embodiment is mentioned in which the light plane generating module is inserted through the working channel of an endoscopic device and manually manipulated. In this implementation the light plane position and orientation (pose) cannot be pre-calculated, therefore measurements made with this embodiment suffer from the same sources of inaccuracy as those described above for other diagnostic and surgical tools inserted through working channels. This also applies to tools inserted through trocars, typically used in laparoscopic surgery.

It is therefore a purpose of the present invention to provide a method for determining the position and orientation of a manually-operated tool in an endoscopic image.

It is another purpose of the present invention to provide a method for determining the position and orientation and providing visual feedback for adequate positioning of a manually-operated light plane endoscopic measurement tool.

It is another purpose of the present invention to provide medical tools comprising integrated light plane measurement capabilities for insertion through working channels of endoscopic devices and through trocars.

Further purposes and advantages of this invention will appear as the description proceeds.

SUMMARY OF THE INVENTION

In a first aspect the invention is a method of determining the position and orientation of a manually-operated endoscopic tool relative to a camera focal point in an endoscopic image. The method comprises:

a) identifying in the image features on the tip of the tool, wherein the features are at least one of salient features of the tip of the tool or features of an imprinted or engraved pose pattern created on the surface of the tip; and b) using a method of camera pose estimation to determine the position and orientation of the features in a 3D camera coordinate system, and therefore the position and orientation of the tool itself.

In embodiments of the method of the first aspect the method of camera pose estimation is the Perspective-n-Point method, for the case of three feature points or more.

In embodiments of the method of the first aspect the tool is a light plane generating module.

In a second aspect the invention is a method of using a manually-operated tool introduced to a site inside a lumen of a body through a working channel of an endoscopic device or through a trocar to make accurate estimates of the dimensions of an object seen in images taken by an endoscopic camera. The method comprises:

a) placing the tool next to the objects;

b) providing a processor device and software configured to analyze the camera images in order to:

i) identifying in the image features on the tip of the tool, wherein the features are at least one of salient features of the tip of the tool or features of an imprinted or engraved pose pattern created on the surface of the tip;

ii) using a method of camera pose estimation to determine the position and orientation of the features in a 3D camera coordinate system, and therefore the position and orientation of the tool itself; and iii) using augmented reality techniques to superimpose on the camera image a virtual ruler at the tip of the tool in contact with the object to obtain accurate estimates of the dimensions of the object.

In a third aspect the invention is a method of using a manually-operated light plane generating module introduced to a site inside a lumen of a body through a working channel of an endoscopic device or through a trocar to make accurate measurements of the dimensions of an object seen in images taken by an endoscopic camera. The method comprises:

a) providing the light plane generating module with distinctive features, wherein the features are at least one of salient features of the light plane generating module or features of an imprinted or engraved pose pattern created on its surface;

b) introducing the light plane generating module until its tip is visible in the endoscopic image;

c) aligning the light plane across the object to be measured;

d) providing a processor device and software configured to analyze the camera images in order to:

i) identify in the image features on the tip of the light plane generating module, wherein the features are at least one of salient features of the tip of the tool or features of an imprinted or engraved pose pattern created on the surface of the tip;

ii) use a method of camera pose estimation to determine the position and orientation of the features in a 3D camera coordinate system, and therefore the position and orientation of the light plane generating module and the offset of the light plane from the camera focal point in the 3D camera coordinate system;

iii) determine the exact coordinates in the 3D camera coordinate system of pixels on the curves formed by intersection of the light plane with the object; and iv) use the known 3D camera coordinates of pixels in the image to determine the actual dimensions of the object.

In embodiments of the method of the third aspect augmented reality techniques are used to superimpose on the camera image a virtual tape measure with ticks along the intersection curves to assist in the visualization of the measurements.

In embodiments of the method of the third aspect the processor device and software are configured to determine the offset of the light plane from the camera focal point and to provide audible or visual feedback for adequate positioning of a manually-operated endoscopic light plane measurement tool. In these embodiments feedback for adequate positioning of the light plane can be provided to the operator in at least one of the following ways:

a) the measurement process is disabled and an audible signal and or a visual message on the display is sent to the operator indicating that the measurement cannot be performed because features are not visible or the offset is below a predetermined threshold;

b) textual or audible messages indicating the expected accuracy; and c) color-coding the display to notify the user of the accuracy of the measurement.

In a fourth aspect the invention is a diagnostic or therapeutic endoscopic tool comprising an attached light plane generating module to provide the tool with integrated light plane measurement capabilities. In embodiments of the diagnostic or therapeutic endoscopic tool the light plane generating module is attached to the tool in one of the following ways: externally, embedded, and completely integrated.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

It is noted that the terms "endoscope" and "endoscopic device" are used herein in a generic sense to apply to endoscopes, catheters, laparoscopes, and similar instruments used in medical applications and also to borescopes and similar instruments used in non-medical applications. Since the word endoscope is usually associated with medical applications, the invention will be described herein in terms of medical endoscopes and procedures but it is to be understood that all of the description and examples given herein apply mutandis mutatis to non-medical endoscopic devices and procedures.

Endoscopic tools are typically introduced to an observation or operating site inside a body lumen through a working channel of an endoscopic device or through a trocar. In order to determine in an endoscopic image the position and orientation of endoscopic tools relative to the camera focal point, it is essential that easily identifiable features on the tip of the tool should be visible in the endoscopic image. The features can either be salient features of the tip of the tool or features of an imprinted or engraved pose pattern created on the surface of the tip to facilitate detection.

Figure 1A:
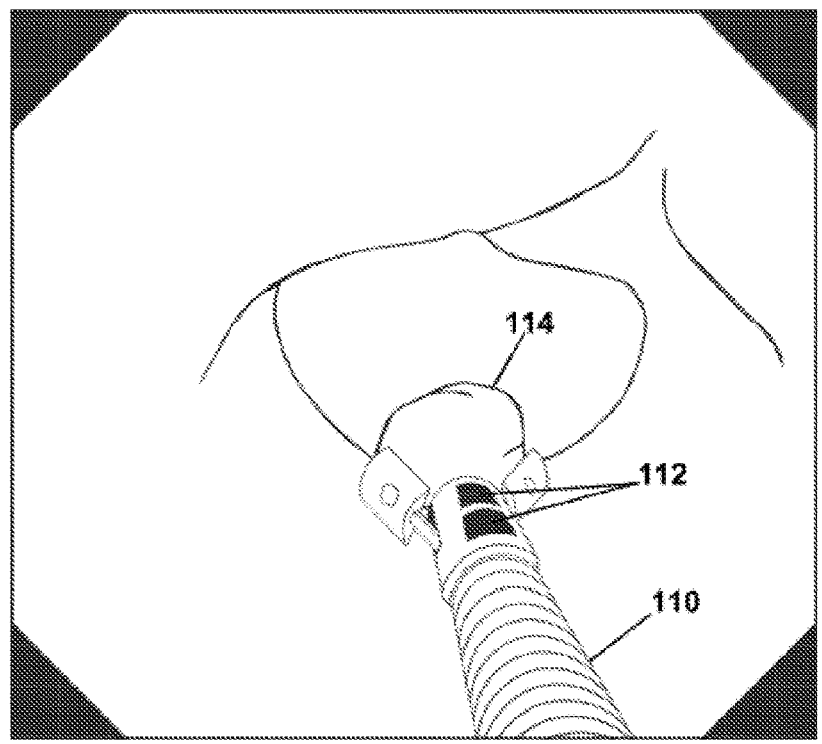
FIG. 1A schematically shows an image gathered by a camera on the endoscope of a biopsy forceps in contact with a polyp.

FIG. 1A schematically shows an image gathered by a camera on the endoscope of a biopsy forceps in front of a polyp. Seen in the figure are biopsy forceps 110 on which a pose pattern 112 has been created, and a polyp 114. It is typically convenient to identify the corners of the pattern as feature points.

If the features that are visible in the image are points, then the Perspective-n-Point method or similar approaches known in the art of camera pose estimation is used to determine their position and orientation in the 3D camera coordinate system, and therefore the position and orientation of the tool itself. Three feature points are used as a minimum, while in practice a fourth feature point and more are used to resolve ambiguity.

Figure 1B:
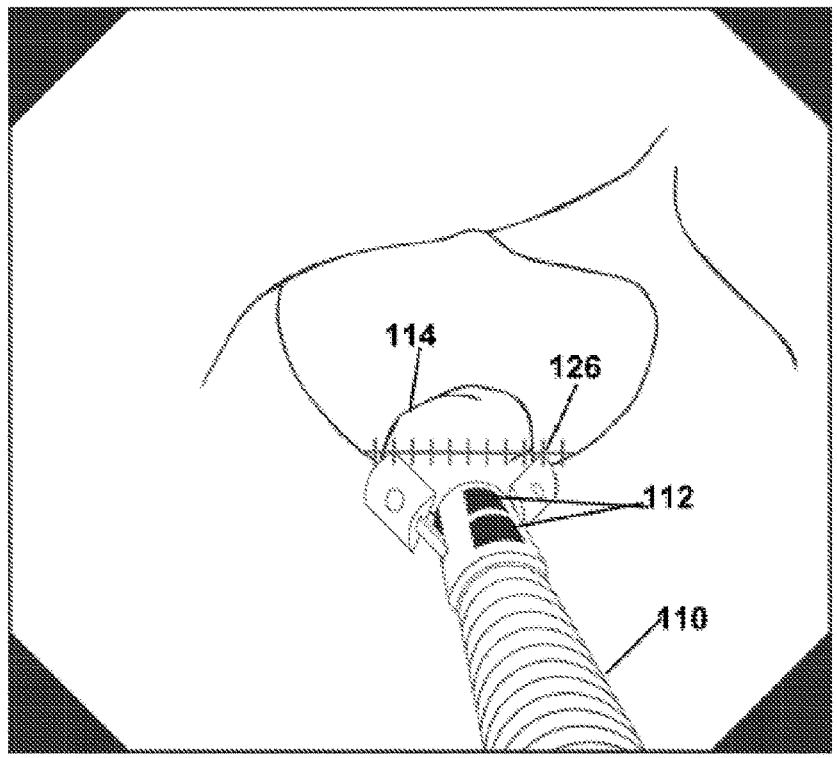
FIG. 1B schematically shows the image of FIG. 1A with a virtual ruler superimposed at the tip of the biopsy forceps.

Any tool that can be introduced to a site inside a lumen of the body through a working channel of an endoscopic device or through a trocar, e. g. forceps, snare, laser, cautery tool, and grasper, can be used to make accurate estimates of the dimensions of objects seen in images taken by the endoscope camera by following the common practice of placing the tool next to the anatomical structure, carrying out the simple procedure above, and providing a processor device and software to analyze the camera images, identify the features and solve the equations of the method used to determine the position and orientation of the tool in the 3D camera coordinate system. Once the position and orientation of the tool in the 3D camera coordinate system is known augmented reality techniques are used to superimpose on the camera image a virtual ruler 126 at the tip of the tool in contact with the object to provide a local scale and more accurate estimates of the dimensions of the object as shown in FIG. 1B.

The method and system described in U.S. Pat. No. 9,545,220 take a simplified approach to solving the problem of measuring, rather than estimating, 3D distances and dimensions of objects in endoscopic images by using a light plane to make linear and geodesic measurements. The endoscopic measurement system of the invention comprises a flexible or rigid endoscopic device equipped with standard endoscopic visualization systems, e.g. a camera, a processing station and components for generating a light plane. Based on triangulation, the intersection curve in an endoscopic image between the light plane and the object of interest is measureable in 3D in the camera coordinate system, much like using an actual tape measure.

Figure 2:
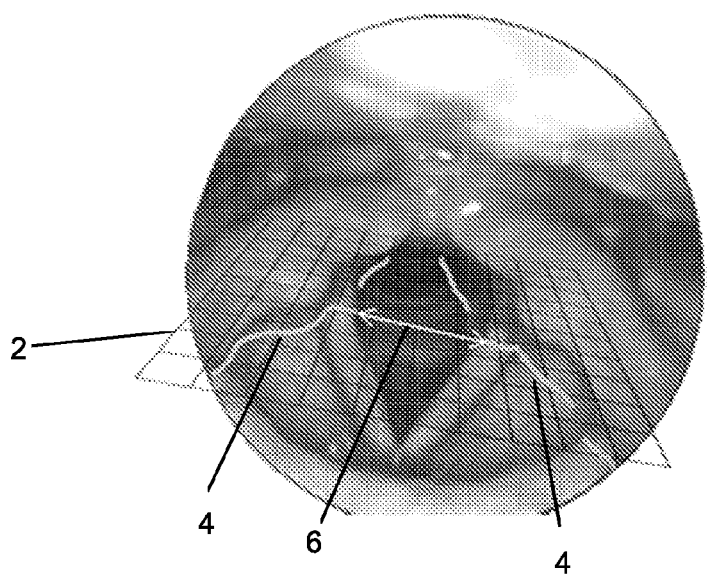
FIG. 2 shows an image of a human larynx imaged using a standard endoscopic visualization system with superimposed features pertaining to the light plane.

FIG. 2 taken from U.S. Pat. No. 9,545,220 shows an image of a human larynx imaged using a standard endoscope. In this image a light plane, is represented by a superimposed reticle 2, the intersection curves of the light plane with the larynx 4, and a measurement of the opening of the vocal cords 6 are schematically illustrated.

Figure 3:
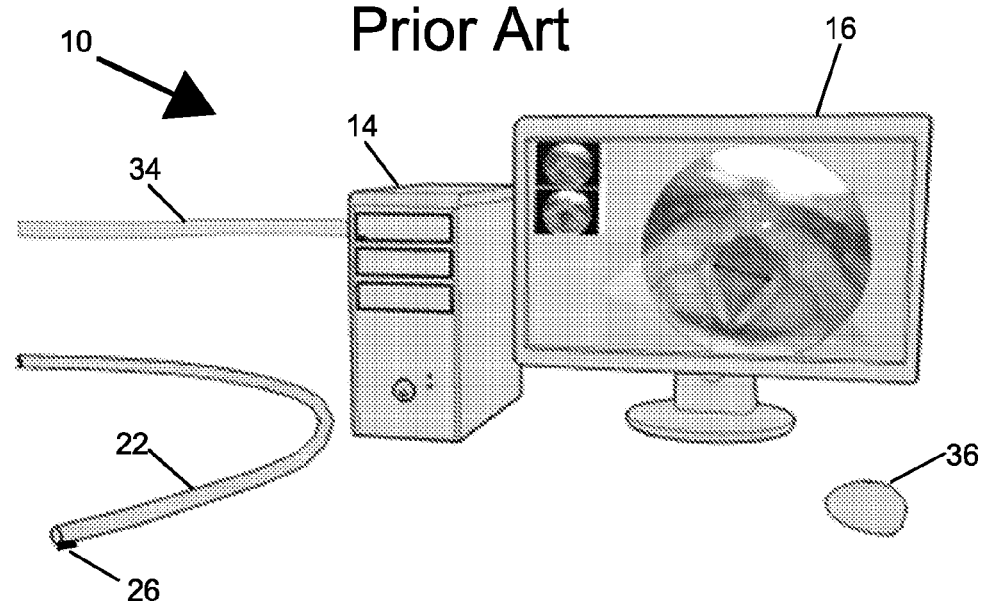
FIG. 3 is a schematic illustration of a specific embodiment of the system of the invention in which a separate processing station is included.

FIG. 3 also taken from U.S. Pat. No. 9,545,220 is a schematic illustration of a specific embodiment of the system of the invention in which a separate processing station is included. The system comprises an endoscopic device that comprises standard endoscopic visualization systems (e.g. a camera) and a light plane generating module 12 attached to the distal end of the endoscopic device 22 and a processing station 10 comprising a processor device 14 that acquires the images from the conventional endoscopy system used to operate the endoscope, and a display 16. Processor device 14 can be, for example, a PC or laptop computer or a Field-Programmable Gate Array or Digital Signal Processor microcontroller. Processor device 14 comprises a dedicated software module that assigns 3D coordinates to each pixel along the intersection curves, a pointing device, and an additional software module implementing a GUI for taking both linear and geodesic measurements at user specified locations. Display 16 presents the images, overlaid graphics and text to the user of the system. The additional software module includes an automatic mode to measure holes or gaps or the diameter of polyps either automatically detected or pointed at by the user on an image displayed on display 16. Also shown in FIG. 3 as components of processing station 10 are cable 34 that transfers images from the conventional endoscopy system connected to the endoscopic device to the processor device 14 and mouse 36, which symbolically represents the pointing device and input devices for user input to the processing station.

In the system illustrated in FIG. 3 the light plane generating module is rigidly attached to the endoscope either as an integrated component or as an add-on unit. In either case the accuracy of the measurements carried out using the light plane is insured by carrying out a calibration procedure as discussed herein above and described in greater detail in U.S. Pat. No. 9,545,220.

Figure 6A:
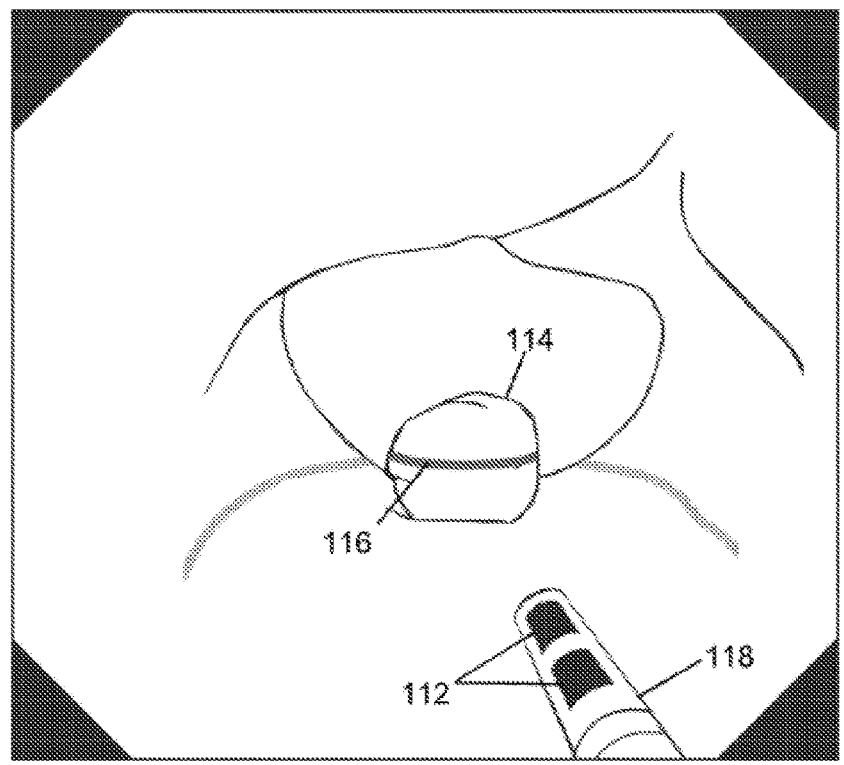
FIG. 6A schematically shows an image gathered by a camera on the endoscope of a tip of a manually-operated light plane generating module in front of a polyp.
Figure 6B:
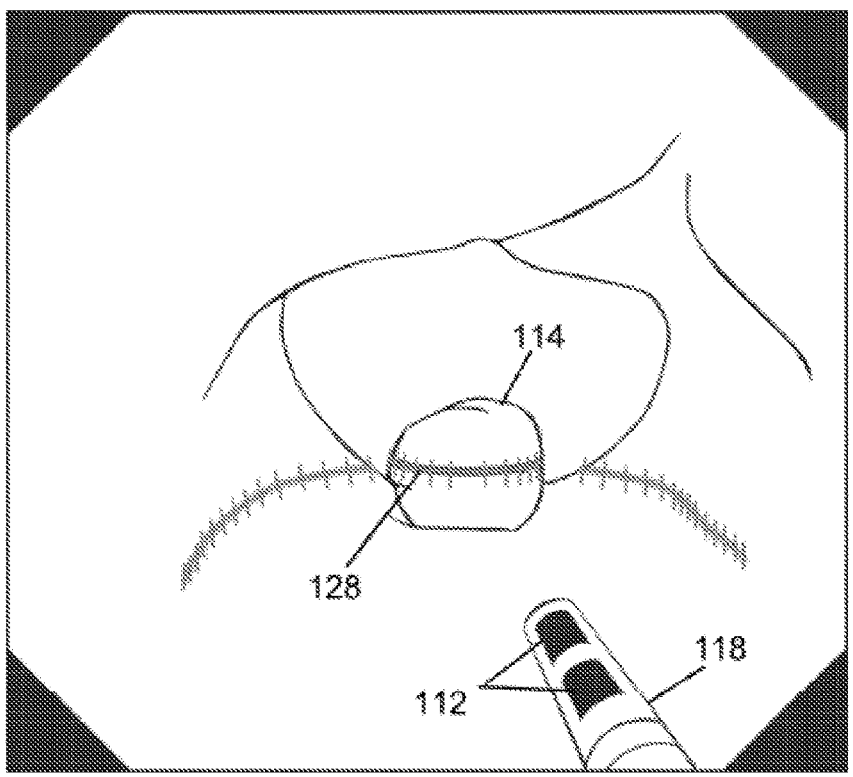
FIG. 6B schematically shows the image of FIG. 6A with a virtual tape measure superimposed on the intersection curves between the light plane and the objects in the scene.
Figure 6C:
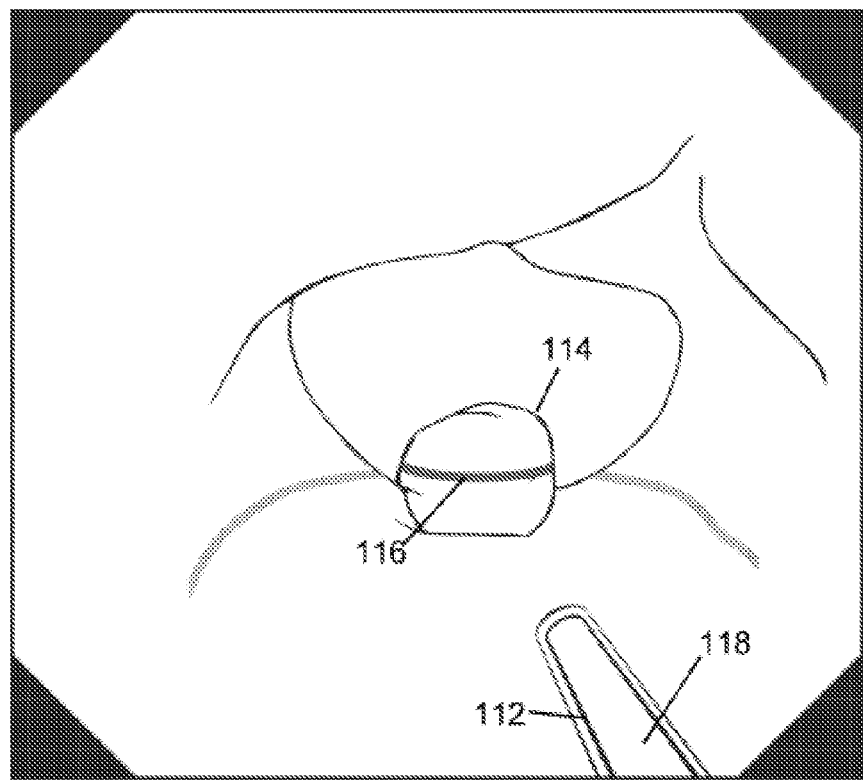
FIG. 6C is the same as FIG. 6A with the exception of the pose pattern on the tip of the tool.

FIG. 6A and FIG. 6C schematically illustrate the present invention in which the light plane generating module 118 is a manually-operated tool introduced through a working channel or a trocar like any other endoscopic tool until its tip is visible in the endoscopic image. Therefore, before the measurements are made, the procedure described herein above is carried out using the pose pattern 112 to determine the position and orientation of the light plane in the coordinate system of the camera in the same way as for any other endoscopic tool as described herein above. In FIG. 6A the pose pattern is composed of two squares. In FIG. 6C the pose pattern is a U-shaped line engraved about the edges of the distal end of the tool. In the case of a light plane generating module however the tool is not in contact with the object, e.g. polyp 114, and no virtual ruler is needed to assess dimensions since the exact coordinates in the 3D camera coordinate system of every pixel on the curves 116 formed by intersection of the light plane with the object are known, which allows accurate measurements to be taken. Once the position and orientation of the manually-operated light plane generating module tool in the 3D camera coordinate system are known augmented reality techniques can be used to superimpose on the camera image a virtual tape measure 128 with ticks along the intersection curves to assist in the visualization of the measurements as shown in FIG. 6B.

The accuracy of a light plane measurement device is dependent on the offset between the light plane and the camera focal point, i.e. if the offset is zero the dimensions cannot be measured and the larger the offset the greater the accuracy. Therefore software in the processor device of the system is configured to determine the position and orientation of the light plane in the 3D camera coordinate system and the offset of the light plane from the camera focal point. The system is also configured to provide audible or visual feedback for adequate positioning of a manually-operated endoscopic light plane measurement tool.

Feedback for adequate positioning can be provided to the operator in several ways, for example:

If not all features are visible such that the measurement cannot be performed or if the offset is below a predetermined threshold then the system is configured to disable the measurement process and send an audible signal and or a visual message on the display.

Provide textual messages indicating whether or not a measurement may be taken, and the expected accuracy.

Color-code the display to notify the user of the accuracy of the measurement. In one exemplary embodiment, Red indicates inability to perform measurement, Orange indicates limited accuracy, Yellow indicates adequate accuracy and Green indicates high accuracy.

Because it is of clinical benefit to accurately measure the size of an object while its histopathology is determined (either in-situ or in the lab) another aspect of the present invention is to integrate light plane measurement capabilities into diagnostic or therapeutic endoscopic tool, such as biopsy forceps and snares, and into in-situ histopathology probes.

Figure 4:
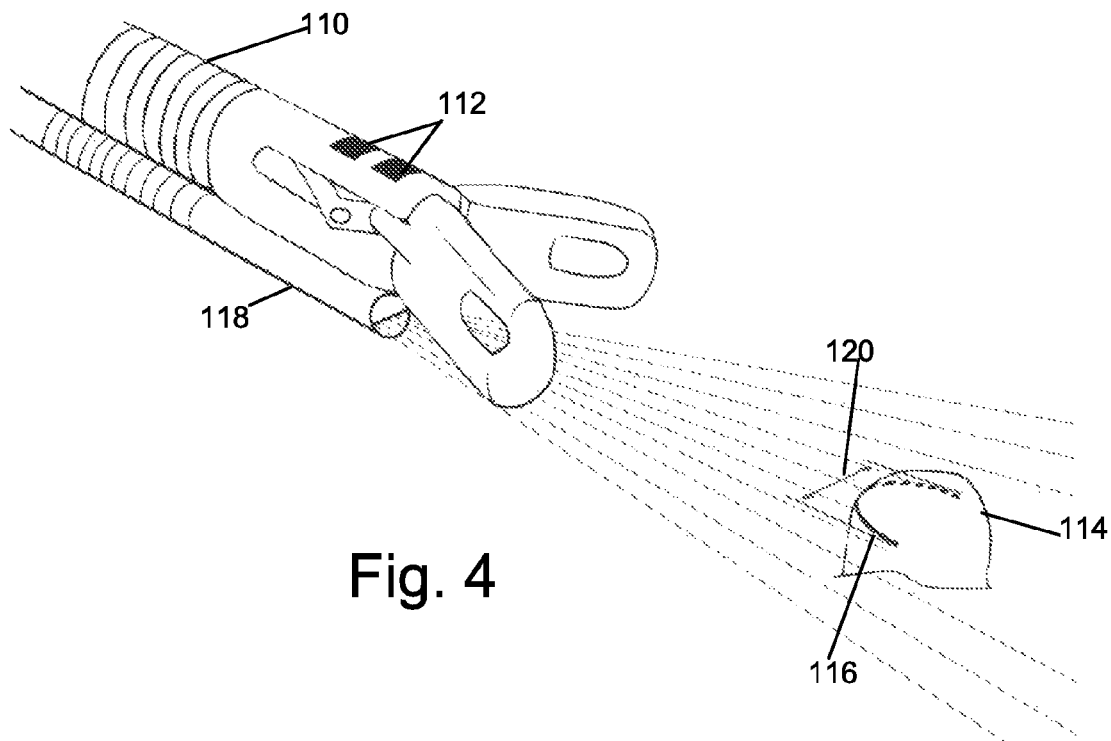
FIG. 4 schematically shows a light plane generating module rigidly attached to a biopsy forceps.

FIG. 4 schematically shows a light plane generating module 118 rigidly attached to a biopsy forceps 110 onto which pose pattern 112 has been created. Also seen in FIG. 4 is a polyp 114, the intersection 116 of the light plane with the polyp, and a double headed arrow 120 that represents the diameter of polyp 114.

Figure 5:
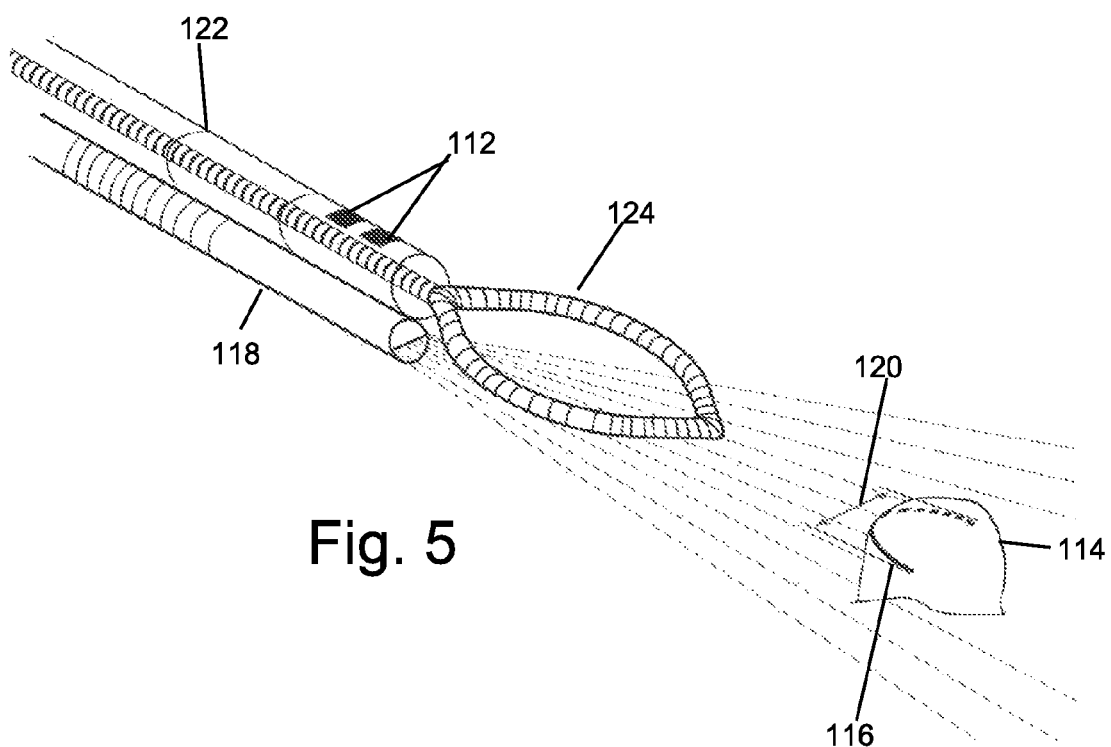
FIG. 5 schematically shows a light plane generating module rigidly attached to the over-tube of a snare.

FIG. 5 schematically shows a light plane generating module 118 rigidly attached to the over-tube 122 of a snare 124 onto which pose pattern 112 has been created. Also seen in FIG. 5 is a polyp 114, the intersection 116 of the light plane with the polyp, and a double headed arrow 120 that represents the diameter of polyp 114.

The light plane generating module can be attached to the tool externally as shown in FIGS. 4 and 5, embedded in an additional lumen in the over-tube of FIG. 5, or in a completely integrated design, e.g. between the jaws of forceps.

Although embodiments of the invention have been described by way of illustration, it will be understood that the invention may be carried out with many variations, modifications, and adaptations, without exceeding the scope of the claims.

The invention claimed is:

1. A method of using a manually-operated light plane generating module introduced to a site inside a lumen of a body through a working channel of an endoscopic device or through a trocar to make accurate measurements of the dimensions of an object seen in an image taken by an endoscopic camera, the method comprising:
   a) providing the light plane generating module with distinctive features, wherein the features are at least one of salient features of the light plane generating module or features of an imprinted or engraved pose pattern created on its surface;
   b) introducing the light plane generating module until the distinctive features are visible in the image;
   c) aligning a light plane generated by the light plane generating module across the object to be measured;
   d) providing a processor device and software configured to analyze the camera images in order to:
      i) identify in the image the features;
      ii) use a method of camera pose estimation to determine the position and orientation of the features in a 3D camera coordinate system, and therefore the position and orientation of the light plane generating module and the offset of the light plane from a focal point of the camera in a 3D camera coordinate system;
      iii) determine exact coordinates in the 3D camera coordinate system of pixels on the curves formed by intersection of the light plane with the object; and
      iv) use known 3D camera coordinates of pixels in the image to determine the actual dimensions of the object.

2. The method of claim 1, wherein augmented reality techniques are used to superimpose on the image a virtual tape measure with ticks along the intersection curves to assist in the visualization of the measurements.

3. The method of claim 1, wherein the processor device and software are configured to determine the offset of the light plane from the focal point of the camera and to provide audible or visual feedback for adequate positioning of a manually-operated endoscopic light plane measurement tool.

4. The method of claim 3, wherein feedback for adequate positioning of the light plane can be provided to the operator in at least one of the following ways:
   a) the measurement process is disabled and an audible signal and or a visual message on a display is sent to an operator indicating that the measurement cannot be performed because the features are not visible or the offset is below a predetermined threshold;
   b) textual or audible messages indicating an expected accuracy; and
   c) color-coding the display to notify a user of the accuracy of the measurement.

5. The method of claim 1, wherein the light plane generating module is attached to a diagnostic or therapeutic endoscopic tool to provide the tool with integrated light plane measurement capabilities.

6. The method of claim 5, wherein the light plane generating module is attached to the tool in one of the following ways: externally, embedded, and completely integrated.

* * * * *